United States Patent [19]

Sher

[11] Patent Number: 5,488,064
[45] Date of Patent: Jan. 30, 1996

[54] BENZO 1,3 DIOXOLE DERIVATIVES

[75] Inventor: Philip M. Sher, Plainsboro, N.J.

[73] Assignee: Bristol-Myers Squibb Company, Princeton, N.J.

[21] Appl. No.: 236,738

[22] Filed: May 2, 1994

[51] Int. Cl.[6] .................. A61K 31/36; C07D 317/68; C07D 405/12
[52] U.S. Cl. .................. 514/465; 549/436; 548/305.1; 548/256; 544/354; 514/397; 514/387; 514/359
[58] Field of Search .................. 514/465, 397, 514/387, 359; 549/436; 548/305.1, 256; 544/354

[56] References Cited

U.S. PATENT DOCUMENTS

| | | |
|---|---|---|
| 3,432,545 | 3/1969 | Howe. |
| 3,501,769 | 3/1970 | Crowther et al.. |
| 4,338,333 | 7/1982 | Ainsworth et al.. |
| 4,772,631 | 9/1988 | Holloway et al.. |
| 5,061,727 | 10/1991 | Bloom et al.. |
| 5,064,863 | 11/1991 | Alig et al.. |

FOREIGN PATENT DOCUMENTS 897118 4/1972 Canada.
52-053-842 4/1977 Japan.

*Primary Examiner*—Nicky Chan
*Attorney, Agent, or Firm*—Ellen K. Park

[57] ABSTRACT

Compounds of the formula

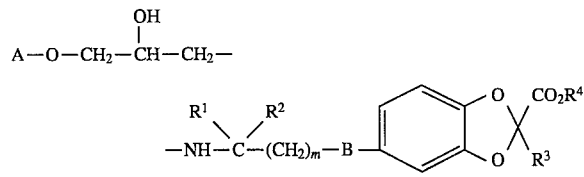

and pharmaceutically acceptable salts thereof where A is phenyl, naphthyl or dihydro- or tetrahydronaphthyl optionally substituted on the aromatic ring by one to three substituents independently selected from halogen, cyano, trifluoromethyl, nitro, alkoxy, alkylsulfonyl, alkyl, cycloalkyl, aryl or a hydrogen bond donor; B is a bond or an oxygen atom and $R^1$ to $R^4$ are as defined herein. These compounds are beta 3 adrenergic receptor agonists and are useful, therefore for example, in the treatment of diabetes, obesity and gastrointestinal diseases.

18 Claims, No Drawings

BENZO 1,3 DIOXOLE DERIVATIVES

BRIEF DESCRIPTION OF THE INVENTION

The present invention is directed to compounds of the formula

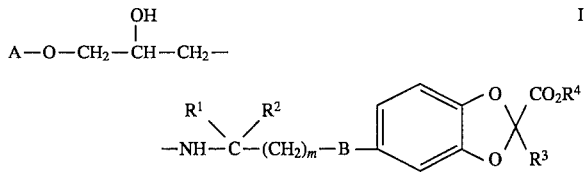

and pharmaceutically acceptable salts thereof. As used in formula I, and throughout the specification, the symbols have the following meanings:

A is phenyl, naphthyl or dihydro- or tetrahydronaphthyl, or these groups optionally substituted on the aromatic ring by one to three substituents independently selected from halogen, cyano, trifluoromethyl, nitro, alkoxy, alkylsulfonyl, alkyl, cycloalkyl, aryl or a hydrogen bond donor;

B is a bond or an oxygen atom;

$R^1$ and $R^2$ are independently hydrogen or lower alkyl;

$R^3$ is hydrogen, lower alkyl or $CO_2R^4$;

$R^4$ is hydrogen or lower alkyl; and m is an integer of 1 or 2.

The compounds of this invention possess activity at the beta 3 adrenergic receptor. The compounds are useful in the treatment of diabetes, obesity, and intestinal hypermotility disorders.

DESCRIPTION OF THE INVENTION

The present invention provides for compounds of formula I, pharmaceutical compositions employing such compounds and for methods of using such compounds. Listed below are definitions of various terms used to describe the compounds of the instant invention. These definitions apply to the terms as they are used throughout the specification (unless they are otherwise limited in specific instances either individually or as part of a larger group).

The term "alkyl" refers to both straight and branched chain groups having 1 to 12 carbon atoms in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like.

The term "lower alkyl" as employed herein includes such alkyl groups as described above containing 1 to 6 carbon atoms.

The term "alkoxy" refers to any of the above alkyl groups linked to an oxygen atom.

Hydrogen bond donating substituents include, but are not limited to hydroxyl, amino, aminocarbonyl, hydroxymethyl, alkylsulfonylamino, acylamino and divalent substituents that render A a benzoheterocycle such as indole, benzimidazole, benzotriazole, benzimidazol-2-one, or quinoxaline-2,3-diol.

The term "aryl" refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1, 2 or 3 lower alkyl groups or halogens.

The term "cycloalkyl" refers to saturated cyclic hydrocarbon groups containing one or more rings of 3 to 12 ring carbons, preferably 3 to 8 ring carbons, which include cyclopropyl, cyclobutyl, cyclopentyl, cyclohexyl, cycloheptyl, cyclooctyl, cyclodecyl, and adamantyl.

The term "halogen" or "halo" refers to fluorine, chlorine, bromine or iodine.

The compounds of formula I can be present as salts, in particular pharmaceutically acceptable salts. The compounds of formula I have at least one basic center, and they can form acid addition salts. These are formed, for example, with strong inorganic acids, such as mineral acids for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, or such as benzoic acid, or with organic sulfonic acids, such as alkane-(of 1 to 4 carbon atoms) or arylsulfonic acids which are unsubstituted or substituted, for example by halogen, for example methane- or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thio-morpholine, piperidine, pyrrolidine, a mono-, di- or tri-lower alkylamine, for example ethyl-, tert-butyl-, diethyl-, diisopropyl-, triethyl-, tributyl- or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form.

It should be understood that the present invention includes prodrug forms of the compounds of formula I.

The compounds of the instant invention may, for example, be in the free or hydrate form, and may be obtained by methods exemplified by the following descriptions.

Compounds of formula I where $R^4$ is hydrogen and in which A contains no reactive substituents (including nucleophilic groups such as hydroxyl and amino and electrophilic moieties such as cyano) are prepared by coupling a compound of formula

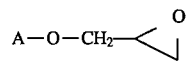

with a compound of formula

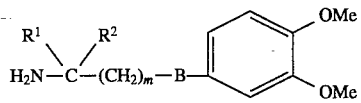

by heating II and III together optionally in the presence of a solvent such as ethanol or by the method described in R.

K. Atkins et al., *Tet. Lett.*, 27, 2451 (1986) to form a compound of formula

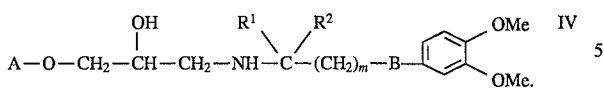

Compounds of formula IV are then reacted with a carbonylating agent such as carbonyldiimidazole in a solvent such as methylene chloride to form compounds of formula

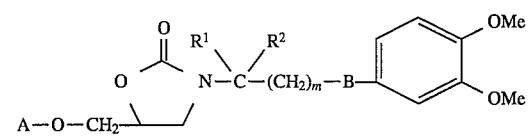

which are then convened to compounds of formula

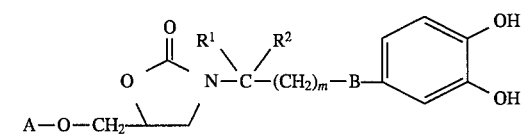

treatment with a Lewis acid such as boron tribromide in a solvent such as methylene chloride or a protic acid such as aqueous HBr and acetic acid.

Compounds of formula VI are then reacted with a dihalide of formula

(where X is chlorine, bromine or iodine) such as diethyl dibromomalonate or dichloroacetic acid (see J. M. Grisar et al., *J. Med. Chem.*, 17, 721 (1974)) in a solvent such as acetone in the presence of a base such as potassium carbonate to form compounds of formula

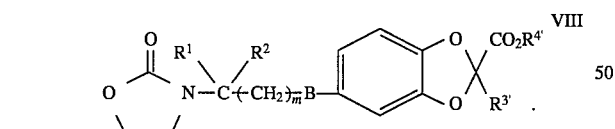

$R^{3'}$ and $R^{4'}$ are defined as $R^3$ and $R^4$, respectively. Compounds of formula VIII are then hydrolyzed for example by heating in concentrated aqueous sodium hydroxide or by the method described in P. G. Gassman et al., *J. Am. Chem. Soc.*, 98 1275 (1976) to form the compounds of formula I where $R^4$ is hydrogen.

Compounds of formula I where $R^4$ is hydrogen and in which A contains reactive substituents such as hydroxyl may be prepared by a parallel route starting with

in which A' is defined A with the reactive substituent masked or in precursor form. For example, hydroxyl may be masked as para-toluenesulfonyloxy. Following the procedures described above for conversion of II to IV to V to VI to VIII to I in the case where the masked substituent is para-toluenesulfonyloxy provides I directly since the hydroxyl group is liberated in the last (hydrolysis) step. Similarly, hydroxymethyl may be masked as 2,4,6-trimethylbenzoyloxymethyl, and where A is indolyl, A' is N-phenylsulfonylindolyl. Other suitable masking groups may be found in Protective Groups in Organic Synthesis by T. W. Greene (John Wiley & Sons). In other cases the procedures provide compounds of formula

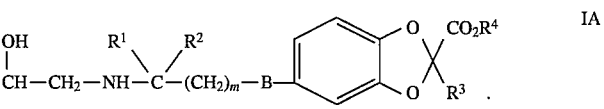

instead of I, where $R^4$ is hydrogen. In these cases, IA is converted to I where $R^4$ is hydrogen by one or more steps in which the reactive substituent is derived from the precursor form. For example, to prepare the compounds in which A is aminophenyl, A' is nitrophenyl and IA is converted to I by hydrogenation over Raney Nickel catalyst in a solvent such as ethanol or tetrahydrofuran.

To prepare the compounds of formula I in which A is acylaminophenyl, A' is nitrophenyl and IA is converted to I by first converting the nitrophenyl group to an aminophenyl group as described above and then convening the aminophenyl group to an acylaminophenyl by treating with an acyl chloride or the corresponding pentafluorophenyl ester in an acidic medium such as aqueous hydrochloric acid solution or an organic solvent, such as N,N-dimethylformamide, containing a strong acid, such as p-toluenesulfonic acid.

Compounds of formula I in which A is

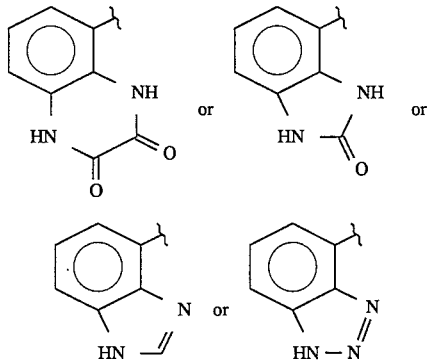

are prepared from compounds of formula IA where A' is 2,3-dinitrophenyl, by first reducing the 2,3-dinitrophenyl to 2,3-diaminophenyl and then construction of the heterocycles by methods described in U.S. Pat. No. 4,310,527 and U.S. Pat. No. 4,346,093.

To prepare the compounds of formula I in which A is cyanophenyl, A' is bromophenyl or iodophenyl and IA is converted to I by radical cyanation, for example, by heating with tri-n-butyltin chloride, sodium cyanoborohydride, 2,2'-azobis(isobutyronitrile), and tert-butyl isocyanide in tert-butanol solution. Other methods for the conversion of IA to I, such as by treatment with potassium cyanide in the presence of a palladium catalyst, are found in the volumes of Compendium of Organic Synthetic Methods, Section 190 (John Wiley & Sons) and in D. M. Tschaen et al., *Synth. Comm.* 24, 887 (1994).

To prepare the compounds of formula I in which A is aminocarbonylphenyl, A' is bromophenyl or iodophenyl and IA is converted to I by first converting the bromophenyl or iodophenyl group to a cyanophenyl group as described described above for the coupling of II with III to provide compounds of formula

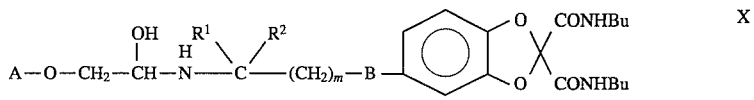

above and then converting the cyanophenyl group to an aminocarbonylphenyl by methods described in the volumes of Compendium of Organic Synthetic Methods, Section 88 (John Wiley & Sons), such as treatment with potassium hydroxide in tert-butanol or with aqueous hydrochloric acid solution.

The compounds of formula I, particularly those in which A is alkoxyphenyl, ,nay be prepared by coupling of II with amine

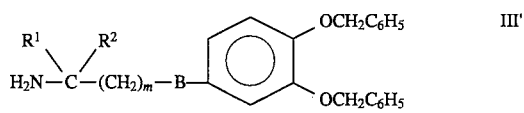

in which the catechol is protected as the dibenzyl ether. The subsequent synthetic steps are analogous to those described above for the conversion of II to IV to V to VI except that

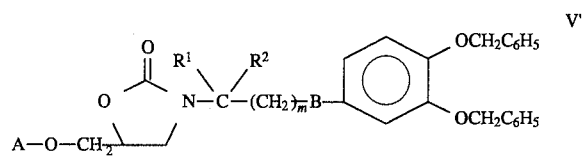

is converted to VI by catalytic hydrogenation in a solvent such as ethanol, ethyl acetate, or acetic acid over a catalyst such as palladium on carbon or palladium hydroxide on carbon.

Another optional modification of the routes described above involves protection of the ethanolamine moiety of IV as the N-acetyl derivative

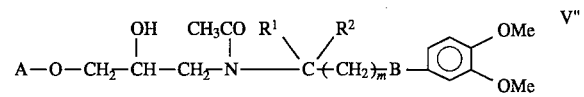

rather than as the oxazolidinone V. The synthetic steps are analogous to those described above for the conversion of V to VI to VIII to I except that compounds

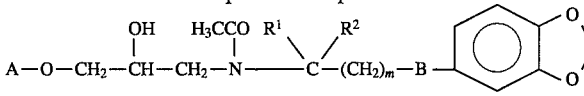

are more easily hydrolyzed to provide the compounds of formula I. The compounds of formula V" are prepared from the compounds of formula IV by treatment with an acetylating agent such as acetic anhydride in a solvent such as methylene chloride in the presence of a scavenger base such as pyridine.

An additional modification of the synthetic route employs intermediate

to prepare the compounds of formula I in which $R^3$ is $CO_2R^4$. A compound of formula IX is coupled with II as which are hydrolyzed to the compounds of formula I by the methods described above for the hydrolysis of VIII.

The compounds of formula IX are prepared from the compounds of formula III by the following reaction sequence: 1. acylation of the amine with 2,2,2-trichloroethyl chloroformate in the presence of a base such as sodium hydroxide or pyridine; 2. bisdemethylation with boron tribromide in a solvent such as methylene chloride; 3. catechol alkylation with diethyl or diisopropyl dibromomalonate in a solvent such as acetone in the presence of a base such as potassium carbonate; 4. diester to diamide conversion by treatment with butylamine; and 5. amine deprotection by reduction with zinc in acetic acid.

It is recognized that various permutations of the modified synthetic routes described above are possible. For example, intermediate IX may be coupled with IIA if A contains a reactive substituent rather than II. In another example, the ethanolamine substructure may be protected as an acetamide (see V") while the catechol is protected as a dibenzyl ether (see III').

To prepare the compounds of formula I where $R^4$ is lower alkyl the compounds of formula I where $R^4$ is hydrogen are esterified by treatment with an alcohol in the presence of a strong acid such as hydrochloric or sulfuric acid.

Compounds of formula II and IIA are available in optically active form by the methods described in J. M. Klunder et al., *J. Org. Chem.*, 54, 1295 (1989).

Compounds of formula III are known compounds or are prepared by methods known in the art. For example, the compounds of formula III where B is a bond, m is 1, and $R^1$ and $R^2$ are not both lower alkyl are prepared by methods described in H. B. Hass et al., *J. Org. Chem.*, 15, 8 (1950). Where $R^1$ is hydrogen and $R^2$ is lower alkyl, these compounds are prepared in optically active form by the methods described in D. E. Nichols et al., *J. Med. Chem.*, 16, 480 (1973).

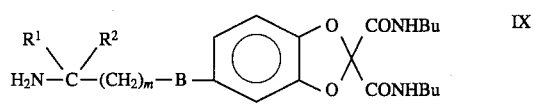

The compounds of formula III where B is a bond, m is 1, and $R^1$ and $R^2$ are both lower alkyl are prepared by the methods described in B. Renger, *Archiv der Pharmazie*, 316, 193 (1983) or U.S. Pat. No. 4,276,304 or D. E. Nichols, *J. Med. Chem.*, 25, 530 (1982).

The compound of formula III where B is a bond, m is 2, and $R^1$ and $R^2$ are hydrogen is known (J. B. Bremmer et al., *Aust. J. Chem.*, 33, 1323 (1980)).

The compounds of formula III where B is a bond, m is 2, $R^1$ is hydrogen and $R^2$ is lower alkyl are prepared by the methods described in F. A. B. Aldous, *J. Med. Chem.*, 17, 1100 (1974).

The compounds of formula III where B is a bond, m is 2, and $R^1$ and $R^2$ are both lower alkyl are prepared analogously to 4-methoxy-α,α-dimethylbenzenepropanamine for example by the methods described in W. Buchowiecki et al., *Tet. Lett.* 26, 1245 (1985).

The compound of formula III where B is an oxygen atom, m is 2, and $R^1$ and $R^2$ are hydrogen is known (K. Mitani et al., *Chem. Pharm. Bull.*, 36, 373 (1988))

The compounds of formula III where B is an oxygen atom and m is 2 are prepared from compounds of formula

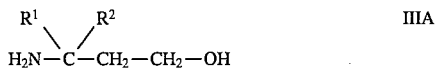

IIIA by 1) protection of the amino group, for example as the tert-butoxycarbamate; 2) activation of the hydroxyl group, for example by tosylation; 3) displacement of the activated hydroxyl with 3,4-dimethoxyphenol in the presence of a base, such as potassium carbonate or sodium hydride; and 4) deprotection of the amino group, for example with trifluoroacetic acid.

The compounds of formula III where B is an oxygen atom, m is 1, and $R^1$ and $R^2$ are not both lower alkyl are prepared by the methods described in A. Waefelaer et al., *Bull. Soc. Chim. Belg.*, 85,421 (1976).

The compounds of formula III where B is an oxygen atom, m is 1, and $R^1$ and $R^2$ are both lower alkyl are prepared by alkylation of 3,4-dimethoxyphenol with a haloacetonitrile such as bromoacetonitrile in the presence of a base such as potassium carbonate in a solvent such as acetone or N,N-dimethylformamide to provide 3,4-dimethoxyphenoxy-acetonitrile which is then reacted with an equivalent of alkyllithium or a Grignard reagent followed by a second equivalent of an optionally different alkyllithium or Grignard reagent according to procedures known for conversion of α-oxygenated nitriles to tertiary amines as exemplified in R. Amouroux and G. P Axiotis, *Synthesis* 270 (1981) and M. Chastrette et al., *Tet. Lett.* 23 (1977).

The compounds of formula III' are prepared analogously to the compounds of formula III or are known in the literature. In some instances reaction conditions are modified in a manner known to those skilled in the art. For example, for the preparation of compounds III' where B is a bond, m is 1, and $R^1$ and $R^2$ are not both lower alkyl, the method of Hass may be used, but reduction of oximes is carded out by lithium aluminum hydride reduction rather than catalytic hydrogenation.

Preferred compounds of formula I are those where B is a bond. The most preferred compounds of formula I are those where B is a bond and $R^3$ is $CO_2R^4$.

The compounds of formula I have activity at the beta 3 adrenergic receptor and are therefore useful, for example, in the treatment of diabetes, obesity, and gastrointestinal diseases such as inflammatory bowel disease, irritable bowel syndrome, nonspecific diarrhea, and peptic ulcer.

Thus a composition containing one (or a combination) of the compounds of this invention, may be administered to a species of mammal (e.g., humans) suffering from diabetes, obesity or an intestinal hypermotility disorder as treatment therefor.

A single dose, or two to four divided daily doses, provided on a basis of about 0.1 to 100 mg per kilogram of body weight per day, preferably about 1 to 15 mg per kilogram of body weight per day is appropriate. The substance is preferably administered orally, but intranasal, transdermal and parenteral routes such as the subcutaneous, intramuscular, intravenous or intraperitoneal routes can also be employed.

The compounds of this invention can also be formulated in combination with $beta_1/beta_2$ adrenergic blockers or stimulants.

The compounds of formula I can be formulated for use in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Based on the literature, it is expected that these compounds may be useful for other indications such as treatment of depression and stress, regulation of intraocular pressure, treatment of conditions associated with increased protein breakdown such as during convalescence after surgery, treatment of hypertriglyceridemia, hypercholesterolemia, atherosclerotic and cardiovascular diseases, and increasing high density lipoprotein levels. In addition, it is expected that these compounds may be useful as feed additives for fattening or improving weight gain or increasing lean body mass in animals and may therefore be used to decrease birth mortality and increase post-natal survival rates in animals.

The following examples and preparations describe the manner and process of making and using the invention and are illustrative rather than limiting. It should be understood that there may be other embodiments which fall within the spirit and scope of the invention as defined by the claims appended hereto.

Example 1

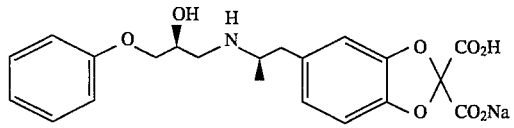

[S-(R*,S*)]-5-[2-[(2-Hydroxy-3-phenoxypropyl)amino] propyl]-1,3-benzodioxole-2,2-dicarboxylic acid, monosodium salt A. [S-(R *,S *)]-1-[[2-(3,4-Dimethoxyphenyl)-1-methylethyl]-amino]-3-phenoxy-2-propanol 1. (S)-(2,3-Epoxypropoxy)benzene The title compound was prepared according to the methods described in J. M. Klunder et al., *J. Org. Chem.*, 54, 1295 (1989). The precursor, (2S)-(+)-glycidyl 3-nitrobenzenesulfonate, to the title compound was recrystallized four times from ethanol to 98.3% e.e. (determined by chiral GC analysis).

2. (R)-3,4-Dimethoxy-α-methylbenzeneethanamine

Prepared as described in D. E. Nichols et al., *J. Med. Chem.*, 16, 480 (1973). The enantiomeric purity of the title compound was calculated to be >99.5% based on the diastereomeric purity of the N-(α-methylbenzyl)-precursor of the title compound as determined by 500 MHz $^1$H NMR and the enantiomeric purity of the α-methylbenzylamine used to prepare it.

3. [S-(R*,S*)]-1-[[2-(3,4-Dimethoxyphenyl)-1-methylethyl]-amino]-3-phenoxy-2-propanol Amine/epoxide couplings mediated by TMS-acetamide are described in R. K. Atkins et al., *Tet. Lett.*, 27, 2451 (1986).

To the title 2 compound (m.w. 195, 2.61 g, 13.4 mmol) at room temperature under argon was added N-(trimethylsilyl)acetamide (1.84 g, 14.0 mmol, 1.04 equiv.). The solution was stirred at room temperature for two hours. To the mixture was then added the title 1 compound (2.0 g, 13.4 mmol, 1.0 equiv.). The resulting solution was then heated at 65°–70° for four days. The mixture was cooled to room temperature and diluted with ~50 mL EtOAc. About 150 mL of chipped ice and 3 mL conc. HCl were added to the solution. After stirring for three hours while warming to room temperature the mixture was basified to pH 12 by addition of 1M aq. NaOH. The ethyl acetate layer was removed, and the aqueous layer was then extracted three times with 100 mL of methylene chloride. All organic extracts were combined and dried over sodium sulfate, and then concentrated to a thick oil, which was purified by silica gel chromatography eluting with 5% (10% conc. aq. $NH_4OH/MeOH)/CH_2Cl_2$ to yield 3.5 g of the title compound (71% yield of monoalkylated product, sample also contains 7% of bis-alkylated material as shown by HPLC and MS), as a clear oil.

TLC: $R_f$=0.5 in 5% (10% conc. aq. $NH_4OH/MeOH)/CH_2Cl_2$, p-anisaldehyde stain, UV. IR: 2920, 1599, 1518, 1246, 1040 cm$^{-1}$. MS: $(M+H)^+$ at 346.

B. [S-(R*,S*)]-3-[2-(3,4-Dimethoxyphenyl)-1-methylethyl]-5-(phenoxymethyl)- 2-oxazolidinone To a solution of the title A compound (3.13 g, 9.1 mmol) in ~150 mL of methylene chloride at room temperature under argon was added triethylamine (1.97 mL, 13.7 mmol, 1.38 g, 1.5 equiv.) and carbonyldiimidazole (2.21 g, 13.7 mmol, 1.5 equiv.) The resulting solution was stirred at room temperature for four days, after which the solution was concentrated and chromatographed on silica gel in 75% EtOAc/hexane to isolate 3.0 g of pure title compound as a white powder, giving an 88% yield.

TLC: $R_f$=0.8 in EtOAc, UV, p-anisaldehyde stain. $^{13}$C NMR (CDCl$_3$): δ5 158.0, 156.9, 149.0, 147.7, 130.2, 129.6, 121.5, 120.9, 114.9, 111.7, 111.0, 70.5, 67.6, 55.9, 55.8, 49.5, 42.5, 39.8, 17.6.

C. [S-(R*,S*)]-3-[2-(3,4-Dihydroxyphenyl)-1-methylethyl]-5-(phenoxymethyl)- 2-oxazolidinone To a solution of the title B compound (1.0 g, 2.7 mmol) in ~100 mL of methylene chloride at 0° C. under argon was added boron tribromide (1.0M in methylene chloride, 20.0 mL, 20.0 mmol, 7.4 equiv.) After stirring at 0° C. for 15 minutes, the reaction was quenched by addition of 15 mL of water. The mixture was extracted three times with 100 mL of methylene chloride. The combined organic extracts were dried over sodium sulfate and concentrated to 850 mg of pure title compound (92%), a brown powder.

TLC: $R_f$=0.5 in 10% MeOH/CH$_2$Cl$_2$, UV, p-anisaldehyde stain. $^{13}$C NMR (CDCl$_3$): δ158.0, 157.9, 144.0, 143.0, 129.6, 129.5, 121.5, 120.8, 115.7, 115.2, 114.4, 71.7, 67.5, 53.4, 42.4, 39.3, 17.4.

D. [S-(R*,S*)]5-[2-[2-Oxo-5-(phenoxymethyl)-3-oxazolidinyl]-propyl]-1,3-benzodioxole-2,2-dicarboxylic acid, diethyl ester To a solution of the title C compound (250 mg, 0.7 mmol) in ~40 mL of acetone at room temperature under argon was added potassium carbonate (503 mg, 3.7 mmol, 5.3 equiv.) and diethyl dibromomalonate (m.w. 318, 254 mg, 0.80 mmol, 1.1 equiv.). The mixture was stirred at room temperature for four days. The mixture was then filtered, concentrated, and chromatographed using a stepwise gradient of 5–50% EtOAc/hexane to isolate the desired product as 187 mg pure title compound (51%).

TLC: $R_f$=0.4 in 20% acetone/toluene, p-anisaldehyde stain, UV. $^{13}$C NMR (CDCl$_3$): δ163.4, 157.9, 156.7, 146.1, 144.6, 132.8, 129.5, 122.9, 121.4, 114.4, 109.6, 108.8, 105.4, 70.7, 67.6, 64.6, 50.0, 42.6, 39.8, 17.2, 13.8.

E. [S-(R*,S*)]-5-[2-[(2-Hydroxy-3-phenoxypropyl)amino]propyl]-1,3-benzodioxole-2,2-dicarboxylic acid, monosodium salt The title D compound (0.46 g, 0.92 mmol) was dissolved with moderate heating in about 30 mL of EtOH and about 34 mL of 0.1M aqueous NaOH solution. The solvent was evaporated to a volume of about 5 mL, and about 40 mL of 10M aqueous NaOH solution was added. A precipitate formed. The mixture was heated to reflux for eight days. After cooling to room temperature, dilution with water did not cause all solid to dissolve. This mixture was chromatographed directly on 20 g of C-18 (from Waters Sep-Pak cartridges) eluting with water. The combined fractions of desired product were neutralized to pH 7.5 with 1.0M aqueous HCl solution A gelatinous precipitate (presumably Na$_2$SiO$_3$) formed. The mixture was again chromatographed as above eluting with water. Desired product containing fractions were combined and evaporated to a small volume. On standing a small amount of precipitate formed; this was removed by decanting. The supernatant was once again chromatographed as above. Again, after evaporation to a small volume, a trace of precipitate was removed by decanting. The supernatant was lyophilized to provide 318 mg (74% yield) of the title compound. Elemental analysis indicated 0.8 moles of sodium.

Analytical HPLC (YMC S-3ODS 6 mm×150 mm column eluting with a 40 min linear gradient starting at 10:90:0.2 MeOH-H$_2$O-phosphoric acid and ending at 90:10:0.2 MeOH-H$_2$O-phosphoric acid with a flow rate of 1.5 mL/min and detection at 217 nm) retention time (min):

| | |
|---|---|
| The title D compound | 35.4 |
| Diacid of the title D compound | 26.2 |
| The title E compound | 17.6 |
| FAB MS in the positive mode: | For (Na, H) M + H$^+$ m/z = 440. |
| | for (H$_2$) M + H$^+$ m/z = 418. |

$[α]_D$=−34° c=0.79 in water. This batch of title compound was derived ultimately from (S)-1,2-epoxy-3-phenoxypropane and (R)-3,4-dimethoxyamphetamine of 98.5% ee and >99.0% ee, respectively.

EXAMPLE 2

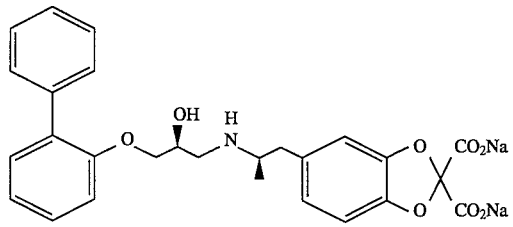

[S-(R*,S*)]-5-[2-[[3-([1,1'-Biphenyl]-2-yloxy)-2-hydroxypropyl]-amino]propyl]-1,3-benzodioxole-2,2-dicarboxylic acid, disodium salt A. (S)-2-(2,3-Epoxypropoxy)[1,1'-biphenyl]

Prepared from o-phenyl phenol in>62% yield using procedures described in J. M. Klander et al., *J. Org. Chem.*, 54, 1295 (1989). The precursor to the title compound, (2S)–(+)-glycidyl 3-nitrobenzenesulfonate was recrystallized four times from ethanol to 99.26% e.e. (determined by chiral HPLC analysis). The title compound was shown to be 98.5% ee by chiral HPLC analysis.

$^{13}$C NMR (CDCl$_3$): δ155, 148, 132, 129, 128, 127, 126, 121,113, 69, 50, 44. TLC: R$_f$=0.5 in 25% EtOAc/hexane, p-anisaldehyde stain, UV.

B. [S-(R*,S*)]-1-([1,1'-Biphenyl]-2-yloxy)-3-[[2-(3,4-dimethoxyphenyl)-1-methylethyl]amino]-2-propanol A mixture of (R)-3,4-dimethoxy-α-methylbenzeneethanamine (prepared as described in step A. 2., of Example 1; m.w. 195, 1.74 g, 8.9 mmol, 2.0 equiv.) and the title A compound (m.w. 226, 1.0 g, 4.4 mmol) was heated under argon overnight at 65°–70° C. The product was purified by silica gel chromatography eluting with 2% (10% conc. aq. NH$_4$OH/MeOH)/CH$_2$Cl$_2$, giving the title compound as 545 mg of a clear oil.

TLC: R$_f$=0.5 in 5% (10% conc. aq. NH$_4$OH/MeOH)/CH$_2$Cl$_2$, p-anisaldehyde stain, UV. $^{13}$C NMR (CDCl$_3$): δ155.4, 148.5, 147.2, 138.2, 131.8, 131.6, 130.9, 129.7, 128.5, 127.7, 126.7, 121.6, 121.2, 112.7, 112.2, 111.0, 71.0, 68.0, 55.6, 54.3, 48.8, 42.7, 19.8.

C. [S-(R*,S*)]-5-[([1,1'-Biphenyl]-2-yloxy)methyl]-3-[2-(3,4-dimethoxyphenyl)-1-methylethyl]-2-oxazolidinone To a solution of the title B compound (m.w. 421,250 mg, 0.59 mmol) in~10 mL of methylene chloride at room temperature under argon was added triethylamine (0.13 mL, 0.09 g, 0.9 mmol, 1.5 equiv.) and carbonyldiimidazole (146 mg, 0.9 mmol, 1.5 equiv.). The solution was stirred for four hours at room temperature and then chromatographed on silica gel eluting with 2% MeOH/CH$_2$Cl$_2$. Pure title compound (219 mg) was isolated as a clear oil (83%).

TLC: R$_f$=0.75 in 5%, MeOH/CH$_2$Cl$_2$, UV, p-anisaldehyde stain.

D. [S-(R*,S*)]-5-[([1,1'-Biphenyl]-2-yloxy)methyl]-3-[2-(3,4-dihydroxyphenyl)-1-methylethyl]-2-oxazolidinone To a solution of the title C compound (m.w. 447, 219 mg, 0.52 mmol) at 0° C. in methylene chloride under argon was added boron tribromide (Aldrich, 10M in hexane, 2.95 mL, 2.95 mmol, 5.7 equiv.). After 45 minutes 50 mL of water was added, the mixture was extracted five times with 50 mL of methylene chloride. The organic extracts were combined, dried (sodium sulfate), and concentrated to 146 mg of pure title compound, as a white solid (67%).

TLC: R$_f$=0.6 in 8% MeOH/CH$_2$Cl$_2$, UV, p-anisaldehyde stain. $^{13}$C NMR (CDCl$_3$): δ157.8, 154.6, 144.1, 143.0, 137.9, 131.1, 130.9, 129.3, 128.7, 128.0, 127.0, 122.0, 120.9, 112.2, 115.7, 115.1, 71.6, 68.2, 50.3, 42.3, 39.1, 17.0.

E. [S-(R*,S*)]-5-[2-[5-[([1,1'Biphenyl]-2-yloxy)methyl]-2-oxo-3-oxazolidinyl]propyl]-1,3-benzodioxole-2,2-dicarboxylic acid, diethyl ester To a solution of the title D compound (m.w. 419, 146 mg, 0.35 mmol) in~3 mL; of acetone at room temperature under argon was added potassium carbonate (m.w. 138,250 mg, 1.8 mmol, 5.0 equiv.) and diethyl dibromomalonate (m.w. 318, 122 mg, 0.39 mmol, 1.1 equiv.). The mixture was stirred for three days before it was filtered and concentrated to 125 mg white oil. Pure title compound (75 mg, 37% yield) was obtained by crystallization from a small volume of EtOH at 0° C. TLC: R$_f$=0.6 in 80% EtOAc/hexane, UV, p-anisaldehyde stain. $^{13}$C NMR (CDCl$_3$): δ163.5, 156.6, 154.8, 146.1, 144.6, 138.3, 132.8, 131.3, 131.0, 129.4, 128.7, 128.0, 127.0 122.9, 122.0, 113.2, 109.7, 108.7, 105, 70.6, 68.2, 63.2, 50.1, 42.3, 39.6, 16.9, 13.9.

F. [S-(R*,S*)]-5-[2-[[3-([1,1'-Biphenyl]-2-yloxy)-2-hydroxypropyl]amino]propyl]-1,3-benzodioxole-2,2-dicarboxylic acid, disodium salt The title E compound (75 mg, 0.13 mmol) was stirred under argon in 9 mL of 5M aqueous NaOH solution. The heterogeneous mixture was refluxed for five days, during which 15 mL more 5M aqueous NaOH was added. The mixture was cooled to room temperature and loaded directly onto a Waters 5 g C-18 Sep-Pak cartridge. The cartridge was eluted with water, then 50% MeOH in water. Relevant fractions were combined and evaporated to obtain 103 mg of a white powder. The solid was repeatedly extracted with DMSO by stirring, followed by centrifugation and supernatant removal. The combined supernatants were lyophilized to provide the title compound.

Analytical HPLC (YMC S-3 ODS 6 mm×150 mm column eluting with a 25 minutes linear gradient starting at 10:90:0.2 MeOH-H$_2$O-phosphoric acid and ending at 90:10:0.2 MeOH-H$_2$O-phosphoric acid with a flow rate of 1.5 mL/minute and detection at 217 nm) retention time (minutes):

| | |
|---|---|
| The title E compound | 27.7 |
| Diacid of the title E compound | 24.3 |
| The title E compound FAB MS in the positive mode: | 21.3 For (Na$_2$) M + H$^+$ m/z = 538. for (Na, H) M + H$^+$ m/z = 516. for (H$_2$) M + H$^+$ m/z = 494. |

What is claimed is:

1. A compound of the formula

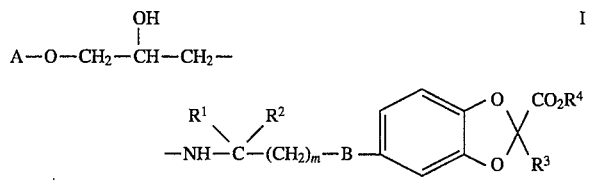

or pharmaceutically acceptable salts thereof where A is phenyl, naphthyl or dihydro- or tetrahydronaphthyl optionally substituted on the aromatic ring by one to three substituents independently selected from halogen, cyano, trifluoromethyl, nitro, alkoxy, alkylsulfonyl, alkyl, cycloalkyl, aryl or a hydrogen bond donor;

B is a bond or an oxygen atom;

R$^1$ and R$^2$ are independently hydrogen or lower alkyl;

R$^3$ is hydrogen, lower alkyl or CO$_2$R$^4$;

R$^4$ is hydrogen or lower alkyl;

m is an integer of 1 or 2; wherein aryl is phenyl or naphthyl optionally substituted with one to three substituents selected from lower alkyl or halogen and a hydrogen bond donor is hydroxyl, amino, aminocarbonyl, hydroxymethyl, alkylsulfonylamino, acylamino and divalent substituents that render A a benzoheterocycle selected from indole, benzimidazole, benzotriazole, benzimidazol-2-one, or quinoxaline-2,3-diol.

2. The compound as recited in claim 1 wherein B is a bond, R$^3$ is hydrogen or lower alkyl, and A contains a hydrogen bond donor.

3. The compound as recited in claim 1 wherein B is a bond, R$^3$ is hydrogen or lower alkyl, and A does not contain a hydrogen bond donor.

4. The compound as recited in claim 1 wherein B is a bond, R$^3$ is CO$_2$R$^4$, and A contains a hydrogen bond donor.

5. The compound as recited in claim 1 wherein B is a bond, R$^3$ is CO$_2$R$^4$, and A does not contain a hydrogen bond donor.

6. The compound as recited in claim 1 wherein B is an oxygen atom, R$^3$ is hydrogen or lower alkyl, and A contains a hydrogen bond donor.

7. The compound as recited in claim 1 wherein B is an oxygen atom, R$^3$ is hydrogen or lower alkyl, and A does not contain a hydrogen bond donor.

8. The compound as recited in claim 1 wherein B is an oxygen atom, $R^3$ is $CO_2R^4$, and A contains a hydrogen bond donor.

9. The compound as recited in claim 1 wherein B is an oxygen atom, $R^3$ is $CO_2R^4$, and A does not contain a hydrogen bond donor.

10. The compound as recited in claim 1 which is [S-(R*, S*)]-5-[2-[(2-hydroxy-3-phenoxypropyl)amino]propyl]-1,3-benzodioxole-2,2-dicarboxylic acid or

[S-(R*,S*)]-5-[2-[[3-([1,1'-biphenyl]-2-yloxy)-2-hydroxypropyl]amino]propyl]-1,3-benzodioxole-2,2-dicarboxylic acid or pharmaceutically acceptable salts thereof.

11. A pharmaceutical composition comprising a compound of claim 1 and a pharmaceutically acceptable carder.

12. A method for treating diabetics comprising administering to a mammalian species in need thereof a therapeutically effective amount of a composition of claim 11.

13. A method for treating obesity comprising administering to a mammalian species in need thereof a therapeutically effective amount of a composition of claim 11.

14. A method for treating gastrointestinal diseases comprising administering to a mammalian species in need thereof a therapeutically effective amount of a composition of claim 11.

15. A pharmaceutical composition comprising a compound of claim 1 in combination with a $beta_1$ or $beta_2$ adrenergic blocker or stimulant and a pharmaceutically acceptable carder.

16. A method for treating diabetes, comprising administering to a mammalian species in need thereof a therapeutically effective amount of a composition of claim 15.

17. A method for treating obesity comprising administering to a mammalian species in need thereof a therapeutically effective amount of a composition of claim 15.

18. A method for treating gastrointestinal diseases comprising administering to a mammalian species in need thereof a therapeutically effective amount of a composition of claim 15.

* * * * *